United States Patent

Downs

[11] Patent Number: 6,123,072
[45] Date of Patent: Sep. 26, 2000

[54] METHOD AND APPARATUS FOR BREATHING DURING ANESTHESIA

[76] Inventor: John B. Downs, 86 Ladoga Ave., Tampa, Fla. 33606

[21] Appl. No.: 08/712,026

[22] Filed: Sep. 11, 1996

[51] Int. Cl.$^7$ ................................................ A61M 16/00
[52] U.S. Cl. ........................... 128/204.21; 128/204.23; 128/204.26; 128/204.18; 128/204.21; 128/205.14; 128/205.18
[58] Field of Search .................. 128/204.23, 204.21, 128/204.25, 204.26, 204.18, 205.18, 205.14, 205.25, 716, 719, 720

[56] References Cited

U.S. PATENT DOCUMENTS

| | | |
|---|---|---|
| 4,773,411 | 9/1988 | Downs . |
| 5,315,989 | 5/1994 | Tobia ................................. 128/204.28 |
| 5,540,220 | 7/1996 | Gropper et al. .................... 128/204.23 |

*Primary Examiner*—Dinh X. Nguyen
*Attorney, Agent, or Firm*—Alan G. Towner; Eckert Seamans Cherin & Mellott, LLC

[57] ABSTRACT

A method and apparatus are provided for ventilation of patients during general anesthesia. Breathing gas is supplied to the patient during anesthesia at a controlled volume above the functional residual capacity of the patient's lungs. The patient is allowed to spontaneously respire when the volume of breathing gas is above the functional residual capacity. The pressure of the breathing gas is periodically reduced to facilitate expulsion of carbon dioxide-containing gas from the patient. The system promotes alveolar ventilation, carbon dioxide excretion, oxygenation and respiratory monitoring in patients who receive general anesthesia.

35 Claims, 5 Drawing Sheets

METHOD AND APPARATUS FOR BREATHING DURING ANESTHESIA

BACKGROUND OF THE INVENTION

1. Field of the Invention

The present invention relates to ventilation of patients during anesthesia, and more particularly relates to a method and apparatus for maintaining and monitoring alveolar ventilation, carbon dioxide excretion and oxygenation in patients who receive general anesthesia.

2. Background Information

General anesthesia induces a state of respiratory insufficiency. Most general anesthetic agents cause a decrease in central drive for respiration, which unimpeded may cause a decrease in oxygenation and increase in arterial blood carbon dioxide tension ($PaCO_2$). In addition, general anesthetic agents decrease respiratory muscle strength. This especially is true of paralytic agents, such as curare, which may remove any ability of the patient to breathe. In addition, general anesthesia has been shown to decrease compliance of the lung and thoracic cage. A decrease in the compliance of these structures requires an increase in muscle strength to produce adequate ventilation, in the absence of mechanical ventilatory assistance.

Anesthetic agents are known to have several effects, which may impede the efficiency of oxygenation. General anesthesia is associated with a decrease in the functional residual capacity (FRC) of the lung, the volume of gas remaining within the lung at the end of normal exhalation. Decrease in FRC will cause a regional decrease in ventilation ($V_A$) relative to perfusion (Q), which may cause decrease in arterial blood oxygenation ($PaO_2$). It has been shown that hypoxic pulmonary vasoconstriction (HPVC) is rendered less active by several anesthetic agents. Release of HPVC will cause an increase in perfusion to poorly ventilated lung units, causing $PaO_2$ to decrease. In addition, it has been shown that the current methodology for delivering positive pressure ventilation will cause flow of gas to be directed to dependent lung regions to a greater extent than to non-dependent lung regions. Yet, gravity directs the flow of blood to more non-dependent lung regions. Therefore, less ventilation and more perfusion will be directed to dependent areas of the lung, causing decrease in $V_A/Q$ and relative arterial hypoxemia (decreased $PaO_2$).

General anesthesia is likely to result in inadequate alveolar ventilation and hypercarbia (increase $PaCO_2$) and inadequate arterial oxygenation (arterial hypoxemia), unless active intervention is applied. For these reasons, positive pressure ventilation is commonly applied to mechanically augment pulmonary ventilation during general anesthesia. In addition, an increase in inspired oxygen concentration is almost always employed, to overcome the arterial hypoxemia producing effects of general anesthesia. Occasionally, a positive end-expiratory pressure (PEEP) is applied to the mechanical ventilatory pattern, in order to increase FRC and improve arterial oxygenation.

Conventional positive pressure ventilation produced with a mechanical ventilator is associated with several undesirable side-effects. Positive pressure ventilation causes physical movement of the lung, chest wall and diaphragm. As a result, any surgical field except for the head, neck and extremities will be subject to undesired movement for a considerable portion of the respiratory cycle. Only during the period of time from end-expiration to initiation of positive pressure breath will the surgical field be still. As mentioned above, both extremes of $V_A/Q$ abnormality will be created by positive pressure ventilation, as created by a standard anesthesia ventilator. An increase in $V_A/Q$ causes increase in alveolar dead space, lung which is ventilated, but not perfused. Decrease in $V_A/Q$ will cause decline in efficiency of oxygenation of the arterial blood. An increase in airway pressure created by positive pressure ventilation will increase intrapleural pressure, decrease venous return and decrease cardiac output. During standard positive pressure ventilation with an anesthesia ventilator, no spontaneous respiratory activity may occur, due to lack of sufficient flow of respiratory gases from the anesthesia circuit. Furthermore, standard positive pressure ventilation from an anesthesia ventilator often results in excessive removal of $CO_2$, increase in arterial blood pH and the well known adverse effects of respiratory alkalosis.

During general anesthesia, monitoring of respiratory function is critically important. Subtle changes in the mechanics of respiration indicate to the anesthesiologist important information with respect to the cardiorespiratory system, such as bronchoconstriction, pulmonary edema and airway obstruction. Changes in pulmonary gas exchange must be monitored for accurate determination of adequacy of alveolar ventilation and oxygenation. Unfortunately, standard mode positive pressure ventilation during general anesthesia with existing equipment makes such monitoring relatively inaccurate and difficult.

Most anesthesia ventilators deliver inspirable gas at a flow rate such that airway pressure is increased excessively, secondary to resistance of the tracheal tube and the patients' large airways. Thus, assessment of small airways resistance is extremely difficult. Institution of an inspiratory hold often is applied to assess airways resistance. However, application of such an inspiratory hold will result in a marked increase in mean airway pressure and intrapleural pressure and decrease in venous return and cardiac output. In addition, such an inspiratory hold significantly decreases the time of stability of the surgical field.

Conventionally, it has been held that the end-tidal carbon dioxide tension ($P_{ET}CO_2$) is an index of alveolar ventilation. Ideally, $P_{ET}CO_2$ is equivalent to $PaCO_2$, but this is true only if all alveoli are perfused and alveolar dead space is non-existent. However, studies have repeatedly shown that positive pressure ventilation applied with a standard anesthesia ventilator tends to cause an increase in alveolar dead space and inaccuracy of monitoring of alveolar ventilation. Therefore, in order to asses adequacy of ventilation during general anesthesia, analysis of arterial blood to measure $PaCO_2$ is necessary.

During the expiratory phase of the respiratory cycle, currently existing means of mechanical ventilation do not allow an active flow of gas from the reservoir bellows. Any flow of gas from the bellows results in a decrease in airway pressure, during the expiratory phase of the respiratory cycle. Thus, any inspiratory effort by the patient during the expiratory phase of the ventilator cycle will result in a decrease in airway pressure. This decrease in airway pressure will cause undesirable decrease in intrapleural pressure, which may cause significant deterioration of cardiovascular function, secondary to afterload of the left ventricle of the heart and will increase work of breathing. For this reason, spontaneous ventilation is not allowed when a mechanical ventilator is employed during general anesthesia. Spontaneous ventilation is permitted only when a standard anesthesia circuit employing a non-encased anesthesia reservoir bag is employed. In addition, anesthesia circuitry does not permit the application of a continuous positive airway pressure (CPAP) during spontaneous respiration. Thus, the only way to maintain a positive airway pressure during the expiratory phase of the respiratory cycle, positive end-expiratory pressure (PEEP), is to maintain complete control of the patients' respiratory function. This causes marked increase in mean airway pressure, mean intrapleural pressure, and significant decrease in venous return and cardiac output. In addition, it has been shown that an increase in mean airway pressure during controlled mechanical ventilation will significantly increase ventilation ($V_A$) relative to perfusion (Q) in many areas of the lung. Such an increase in $V_A/Q$ will increase physiologic dead space, with its attendant undesirable effects.

As detailed above, it is well known and accepted medical practice that patients receiving general anesthesia require mechanical ventilatory support. In almost all cases, this is accomplished using a semi-closed system with a $CO_2$ absorbent that will allow partial rebreathing of anesthetic gases. Some systems employ sufficiently high gas flow to prevent significant rebreathing of anesthetic gases, so that $CO_2$ absorption is unnecessary. Nearly complete rebreathing of anesthetic gases is rarely accomplished without $CO_2$ absorption, but when attempted control of arterial $CO_2$ tension is maintained with a fresh gas flow into the rebreathing circuit in an amount necessary to maintain arterial blood $CO_2$ tension at an acceptable level and a total ventilation of at least 3 times the level of fresh gas inflow. With these systems, a collapsible reservoir of variable capacity is alternately compressed and allowed to relax by application and release of positive pressure from a compressed gas source. Usually, this reservoir consists of a concertina bag, housed within a rigid, clear container. The concertina bag is typically filled from below, so that inspiration to the patient consists of a fall in the bellows secondary to externally applied pressure within the rigid container. Exhalation from the patient results in gas entering the bellows, causing it to rise within the container. The volume of gas delivered by the positive pressure breath is determined by the height of the bellows within the cylinder prior to inspiration and the distance that the bellows travels during the inspiratory phase of the ventilatory cycle. Various means of controlling volume delivery and inspiratory pressure have been devised. These include regulation of flow into the rigid chamber, time allowed for inspiration, and mechanical limitation of the excursion of the bellows.

Various types of ventilators have been developed for patients afflicted with acute lung injury and/or respiratory failure. Among the conventional mechanical ventilation techniques are assist mechanisms, intermittent mandatory ventilation (IMV), positive end-expiratory pressure (PEEP) and high frequency low-tidal volume therapy, such as applied in infant ventilation. U.S. Pat. No. 4,773,411 to Downs, the disclosure of which is incorporated herein by reference, discloses an apparatus for applying continuous positive airway pressure to patients with respiratory disorders. The disclosed apparatus achieves augmentation of alveolar ventilation and carbon dioxide excretion through intermittent cycles of reduced airway pressure below the CPAP pressure level. The apparatus is used to provide ventilatory assistance to patients with impaired spontaneous respiration capability.

Despite the above-noted developments, a need exists for an apparatus and associated method that can, in combination, maintain alveolar ventilation, carbon dioxide excretion and oxygenation in patients during general anesthesia.

SUMMARY OF THE INVENTION

The present invention, referred to as apneustic anesthesia ventilation or AAV, offers a novel and improved method and apparatus for maintaining alveolar ventilation, $CO_2$ excretion and oxygenation to patients who receive general anesthesia. The term "general anesthesia" is used herein in accordance with its conventional meaning and includes the provision of anesthesia to a patient undergoing a surgical procedure. As exemplified herein, the termn "patient" is a member of the animal kingdom including mammals, particularly humans. Such patients may, or may not, require mechanical augmentation of ventilation, but are allowed to breathe spontaneously, if desired. AAV is produced by maintaining elevation of airway pressure by external pressurization of the concertina bag throughout most of the respiratory cycle. Application of pressure to the concertina bag causes the patient's lungs to remain partially inflated at a volume above FRC, which is determined by the level of applied pressure. The applied pressure and resultant increase in lung volume are such that there is little impedance to alveolar blood flow and, therefore, substantially no additional alveolar dead space. Thus, $P_{ET}CO_2$ accurately reflects $PaCO_2$, under normal circumstances. Application of airway pressure is such that the opening pressure of all alveoli is equivalent, whether dependent or independent. Thus, exchange of oxygen between alveolar space and pulmonary capillary blood is unimpeded. Exchange of gas between alveolar air and the anesthesia breathing circuit is accomplished by unrestricted spontaneous respiration, or by intermittent decrease in airway pressure, resulting in a flow of gas from well perfused alveolar spaces to the anesthesia breathing circuit. A standard semi-closed anesthesia circuit insures absorption of all carbon dioxide, so that rebreathing of the anesthetic gases will not cause elevation of $PaCO_2$. Because of the relative lack of alveolar dead space, $CO_2$ elimination is far more efficient than observed with standard mode positive pressure ventilation. Further, because of relative absence of alveolar dead space, end-tidal $CO_2$ monitoring renders analysis of arterial blood for determination of $PaCO_2$ unnecessary, with rare exception. During the expiratory phase of the respiratory cycle, lung and thoracic compliance is determined accurately by dividing the change in lung volume, which occurs with a drop in airway pressure, by the level of applied airway pressure. Since the applied airway pressure is measured at a time of no flow, and since the determination of the change in lung volume during the drop in airway pressure is determined at a period of no flow, determination of compliance of the respiratory system is independent of airways resistance and significantly more accurate than that determined during standard mode positive pressure ventilation during general anesthesia.

By allowing patients to breathe spontaneously during general anesthesia, AAV permits decrease in intrapleural pressure, increase in venous return and maintenance of cardiac output. Spontaneous ventilation permits improved distribution of alveolar ventilation, compared to standard positive pressure ventilation during general anesthesia. Thus, $V_A/Q$ is more normal, allowing improved oxygenation of arterial blood, as well as decrease in physiologic dead space. The latter effect permits more accurate monitoring of alveolar ventilation and reduced requirement for analysis of arterial blood. Because patients may breathe spontaneously, muscle relaxation with paralytic agents is less necessary and a lighter plane of general anesthesia may be used because control of respiration by increased depth of anesthesia is unnecessary. In addition, AAV produces a continuous positive airway pressure (CPAP) so that control of ventilation is unnecessary, in order to provide a positive end expiratory pressure (PEEP), when increase in FRC is desired.

The apneustic anesthesia ventilator may have several controls. There is preferably a mechanism to control the time during which airway pressure and lung volume are increased. An adjustable time will determine how long, if at all, lung volume and airway pressure are decreased to a lesser level. The present invention ensures sufficient flow of gas to the container surrounding the concertina bag, so that any change in volume or pressure demanded by the patient is met with minimal fluctuation in airway pressure. The apparatus preferably includes a demand valve, or continuous flow device, or other such mechanism, to permit unrestricted flow of gas, upon patient demand. A reservoir system may be instituted with a flat pressure response to change in volume. The present invention allows the clinician to adjust pressure and volume levels within the breathing circuit, both up and down, preferably by means of a flow and/or volume sensor on both the inspiratory and expiratory limb of the concertina bag. The clinician may set the desired change in lung volume and/or airway pressure with a feedback mechanism from the flow/volume sensors. The apparatus preferably includes a valve to permit exit of gas from the rigid container surrounding the concertina bag, with sufficiently low resistance to permit exit of gas with no significant change in pressure, secondary to the flow.

An object of the present invention to provide a novel and improved method and apparatus for assisting and improving ventilation of patients undergoing general anesthesia.

Another object of the invention is to provide a method and apparatus which allows improved alveolar ventilation and $CO_2$ excretion and permits maintenance of unrestricted spontaneous breathing during general anesthesia.

A further object of the invention is to provide a means of assisting elimination of carbon dioxide in patients undergoing general anesthesia wherein mediated breaths are induced by reduction of airway pressure below an otherwise continuously maintained positive airway pressure.

Another object of the invention is to provide ventilatory support whereby a continuously maintained positive airway pressure maintains lung volume above FRC, in order to produce apneustic oxygenation and elimination of carbon dioxide from the lung by periodic reduction in lung volume to FRC.

A further object of the present invention is to minimize movement of the surgical field in patients during general anesthesia.

Another object of the present invention is to provide an apparatus and associated method for ventilating patients during general anesthesia without interfering with the surgical procedure.

A further object of the present invention is to provide for monitoring of ventilation during general anesthesia.

A further object of the present invention is to provide a method of supplying breathing gas to a patient during anesthesia, including the steps of providing a supply of breathing gas to the patient, controlling the volume of the breathing gas supplied to the patient at a level above the functional residual capacity of the patient, allowing the patient to spontaneously respire while the volume of breathing gas is above the functional residual capacity of the patient, and periodically reducing the pressure of the breathing gas supplied to the patient to facilitate expulsion of carbon dioxide-containing gas from the patient.

Another object of the present invention is to provide an apparatus for supplying breathing gas to a patient during anesthesia including supply means for providing breathing gas to the patient, control means for controlling the volume of the breathing gas supplied to the patient at a level above the functional residual capacity of the patient, and for periodically reducing the pressure of the breathing gas supplied to the patient to facilitate expulsion of carbon dioxide-containing gas from the patient, and spontaneous breathing means for allowing the patient to spontaneously respire while the volume of the breathing gas is above the functional residual capacity of the patient.

These and other objects of the present invention will become more readily apparent from the following description.

DESCRIPTION OF THE PREFERRED EMBODIMENT

Figure 1:
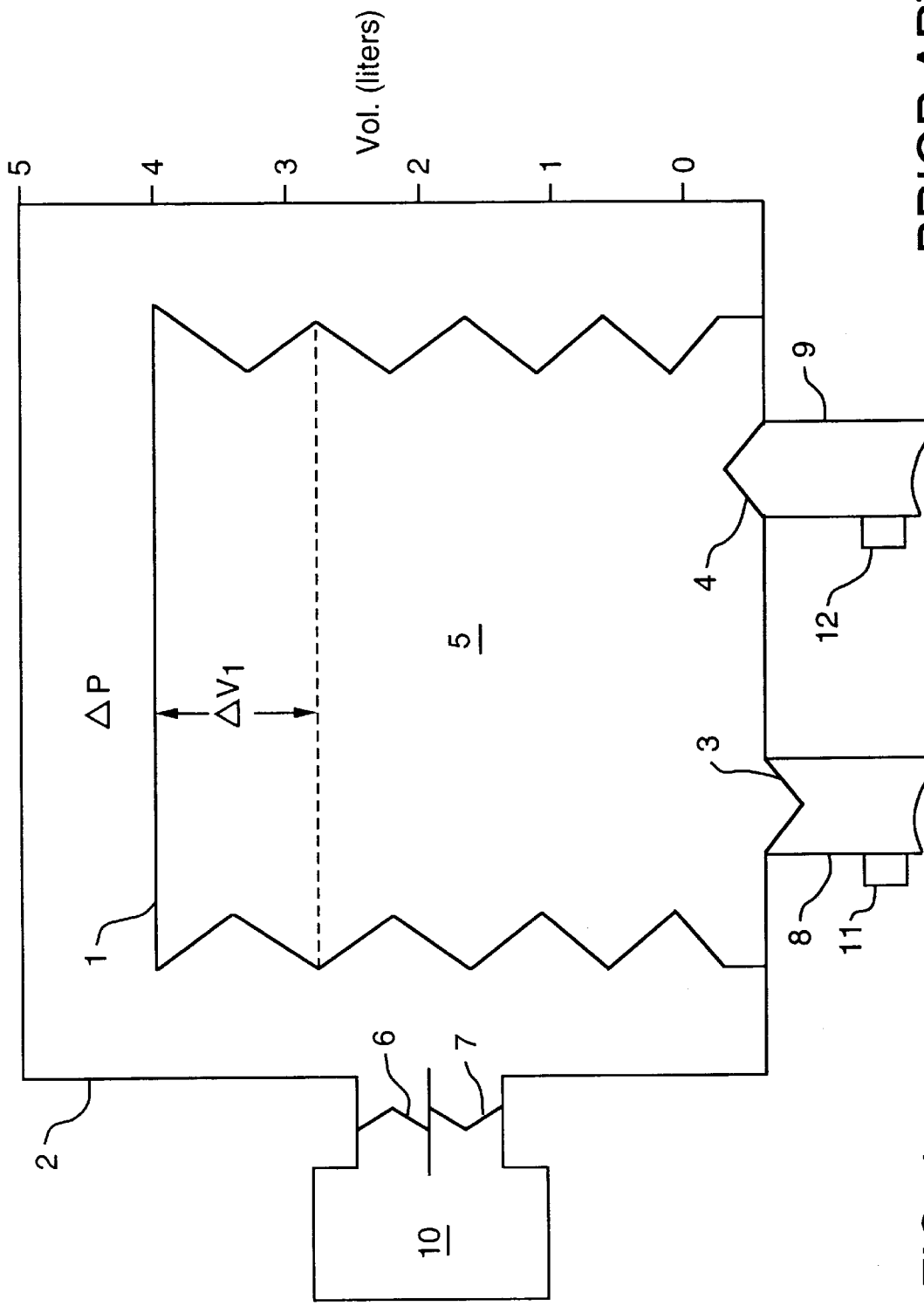
FIG. 1 is a partially schematic illustration of a conventional concertina bag.

Referring to FIG. 1, a conventional concertina bag 1 is contained and sealed within a rigid, translucent container 2. Inspiratory and expiratory flow to and from the concertina bag is directed by unidirectional valves 3 and 4 in inspiratory 8 and expiratory 9 ports, respectively. Movement of the concertina bag 1 and gas volume 5 is determined by intermittent pressurization ($\Delta P$) of the rigid outer container through an inhalation valve 6 and an exhalation valve 7 to permit return of pressure within the translucent container 2 to nearly ambient. An anesthesia ventilator control 10 controls the flow rate of gas into the rigid container, the time of gas flow into the container, and the time from cessation of flow to initiation of flow during the next breath. A pressure limit may be imposed, to limit increase in airway pressure. Inspiratory time may be set, as is expiratory time, to determine respiratory rate. Flow sensors 11 and 12 are placed on the inspiratory 8 and expiratory 9 ports of the concertina bag.

Figure 2:
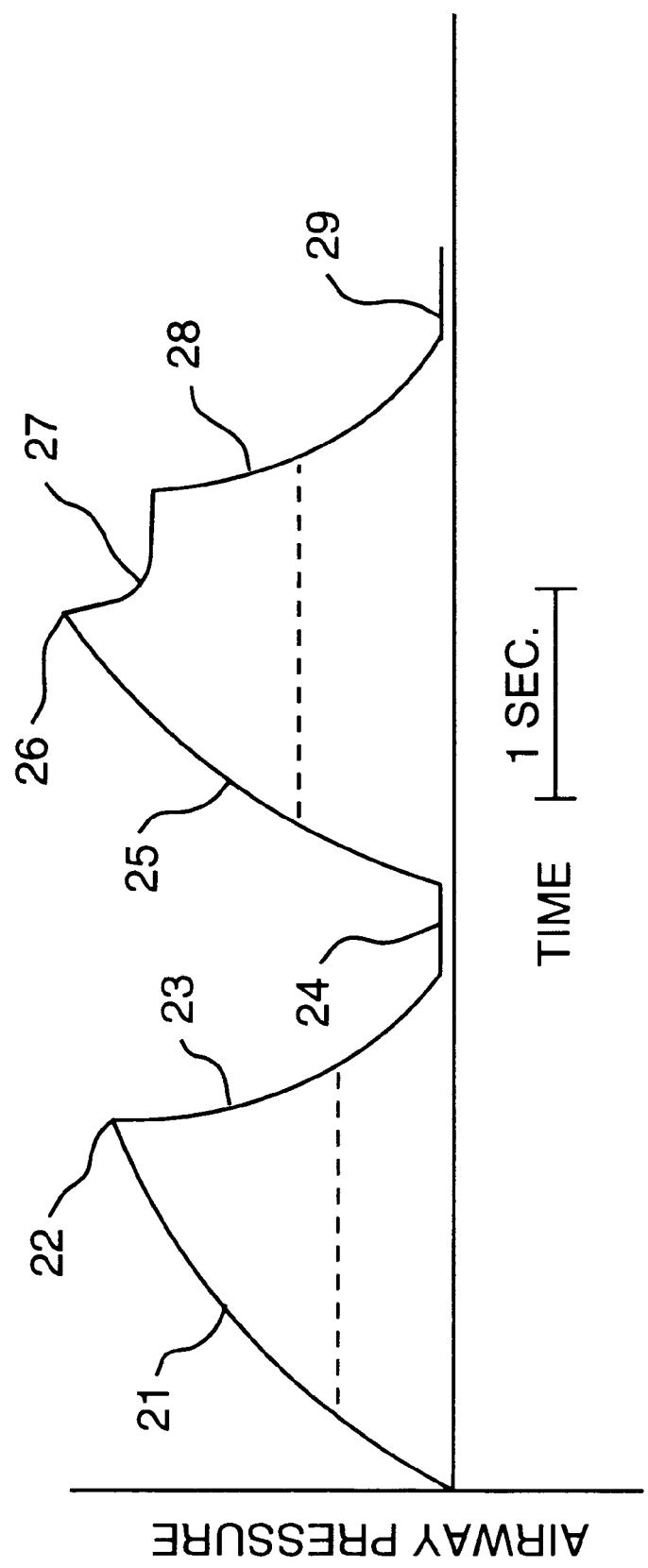
FIG. 2 is a graph of airway pressure vs. time representative of the use of the conventional concertina bag of FIG. 1.

The airway pressure patterns resulting from the use of the conventional apparatus of FIG. 1 are shown in FIG. 2. The ventilator control 10 is a constant pressure generator which compresses the concertina bag 1, resulting in a decelerating flow and tapered airway pressure (Paw) pattern 21 which switches to exhalation 22 at a predetermined time, volume or pressure. Exhalation valve flow resistance causes Paw to decrease, as the lung empties into the breathing circuit, with a decelerating flow and tapered pressure pattern 23. In the absence of an expiratory resistor, expiratory Paw 24 is ambient. A time-cycled inspiratory flow creates an inspiratory Paw rise 25 as lung volume increases and airways resistance results in a peak Paw 26 higher than the Paw created during an inspiratory hold, resulting in a plateau Paw 27 during a period of little or no inspiratory flow. Exhalation 28 is similar to the plateau Paw 27 and expiratory time 29 is generally shorter than the expiratory Paw 24. The latter pattern is most common with current anesthesia ventilator technology and creates a significant increase in inspiratory time and mean airway pressure. The mean airway pressure for each pattern is shown by the dashed lines in FIG. 2.

Figure 3:
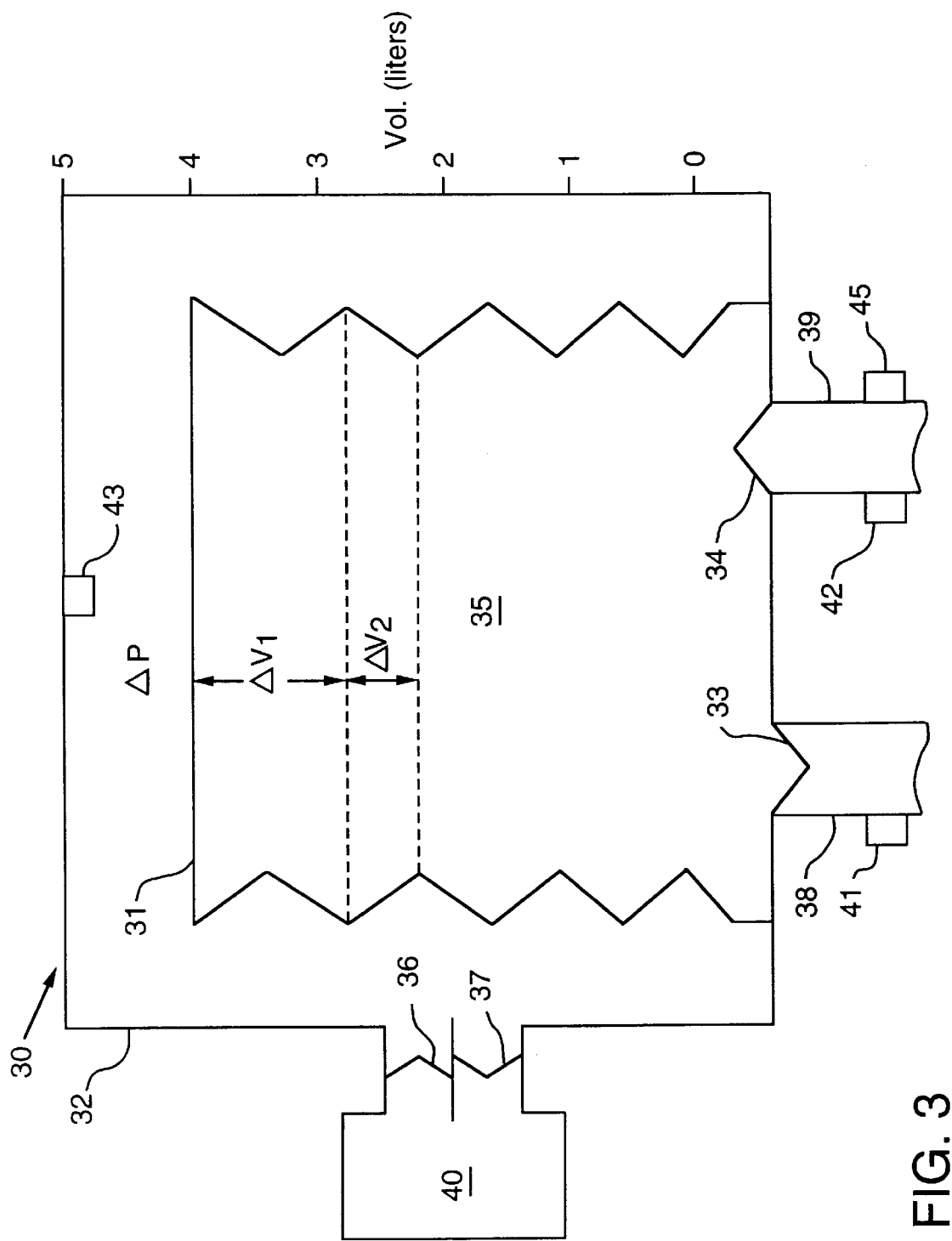
FIG. 3 is a partially schematic illustration of an apneustic anesthesia ventilator in accordance with an embodiment of the present invention.

In accordance with an embodiment of the present invention as shown in FIG. 3, an apneustic anesthesia ventilator 30 includes a reservoir bellows or concertina bag 31 contained within a rigid translucent container 32. Gas may exit the concertina bag 31 to the anesthesia breathing circuit and may enter the concertina bag 31 from the breathing circuit through unidirectional valves, as indicated at 33 and 34, through inspiratory 38 and expiratory 39 ports, respectively. The ventilator 30 may be used in place of conventional ventilators used during anesthesia.

Figure 4:
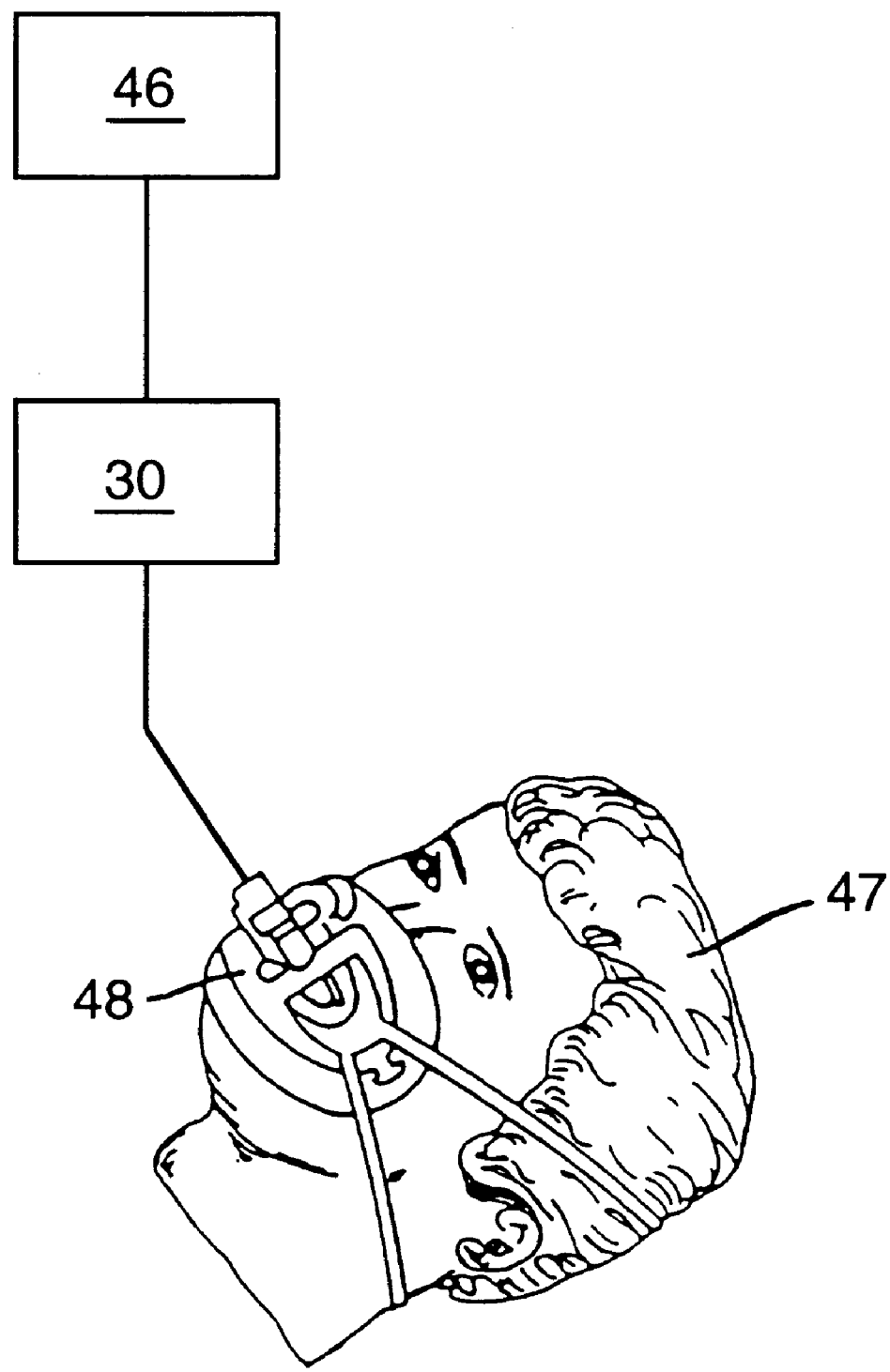
FIG. 4 is a partially schematic illustration of a ventilator of the present invention located between a source of breathing gas and a patient under general anesthesia.

As shown in FIG. 4, the ventilator 30 may be connected in flow communication between an anesthesia gas delivery system 46 and the airway of a patient 47 undergoing a surgical procedure. The anesthesia gas delivery system 46 may be of any suitable design including conventional closed systems and semi-closed systems, such as a semi-closed circle $CO_2$ absorber system or a Mapleson-D system. The ventilator 30 may be connected to the airway of the patient 47 by any suitable means such as a mask 48, tube or laryngeal mask airway (LMA).

Change in lung volume can be quantified by the volume 35 as determined by excursion of the bellows 31 shown in FIG. 3. An AAV control 40 controls ΔP by pressurizing the canister 32 with a flow of gas through valve 36, or by decompressing the canister 32 with a negative pressure applied through valve 37, or positive pressure applied as gas enters the bellows 31 through expiratory valve 34. The AAV control 40 functions to control CPAP level, CPAP time, flow rate, ΔP or release pressure, and release time. Any suitable timer including manually adjustable timers may be used to control CPAP and release times. Any suitable variable pressure source may be used to control CPAP, flow rate and release pressure levels, such as a manually adjustable pressure source. The pressure sensor 43 may be used to verify the pressure level of the system. Cycle time of the system is equal to CPAP time plus release time. The respiratory rate established by the AAV control 40 is equal to the cycle time divided by 60 seconds.

The volume of breathing gas supplied to the patient is controlled at a level above the functional residual capacity of the patient's lungs. Preferably, the volume of breathing gas is about 3 to 6 ml/kg greater than FRC. Flow sensors 41 and 42 are placed on the exit and entry flow paths 38 and 39, respectively. Pressure (ΔP) is developed about the concertina bag 31, within the translucent container 32, by means of flow of gas controlled by the AAV control 40. Change in volume of the concertina bag by entry or exit of gas from the patient's lungs (ΔV) will be determined by change in pressure (ΔP) created by the AAV control 40 and by the patient's own respiratory effort.

As shown in FIG. 3, $\Delta V_2$ represents the volume of gas inhaled and exhaled by the patient's own spontaneous effort, and is not associated with any significant change in airway pressure. The valves 33 and 34 are preferably of sufficient size and shape to prevent any significant resistance to gas flow inspiratory or expiratory. The flow sensors 41 and 42 are preferably placed on both the exit 38 and entry 39 limbs from and to the concertina bag 31, in order to determine flow of gas and to permit calculation of ΔV, and $\Delta V_2$. A pressure measuring device 43 such as an aneroid manometer is preferably included as a part of the breathing circuit and may be an integral part of the flow measuring device, in order to permit calculation of compliance ($\Delta V_1/\Delta P$). An end-tidal carbon dioxide sensor 45 is placed on the expiratory limb 39 of the patient's breathing circuit, in order to measure $P_{ET}CO_2$.

The AAV control 40 determines the amount of gas and applied pressure required to maintain position of the bellows, so that the patient's airway pressure and lung volume are controlled, as desired. The AAV control 40 includes a timing mechanism to determine the duration of application of increased airway pressure, the duration of decrease in airway pressure, the level of airway pressure and the level of decrease in airway pressure. As shown in FIG. 4, control of gases breathed by the patient is determined by a conventional anesthesia machine 46 to which the patient's breathing circuit 38, 39 is connected.

Figure 5:
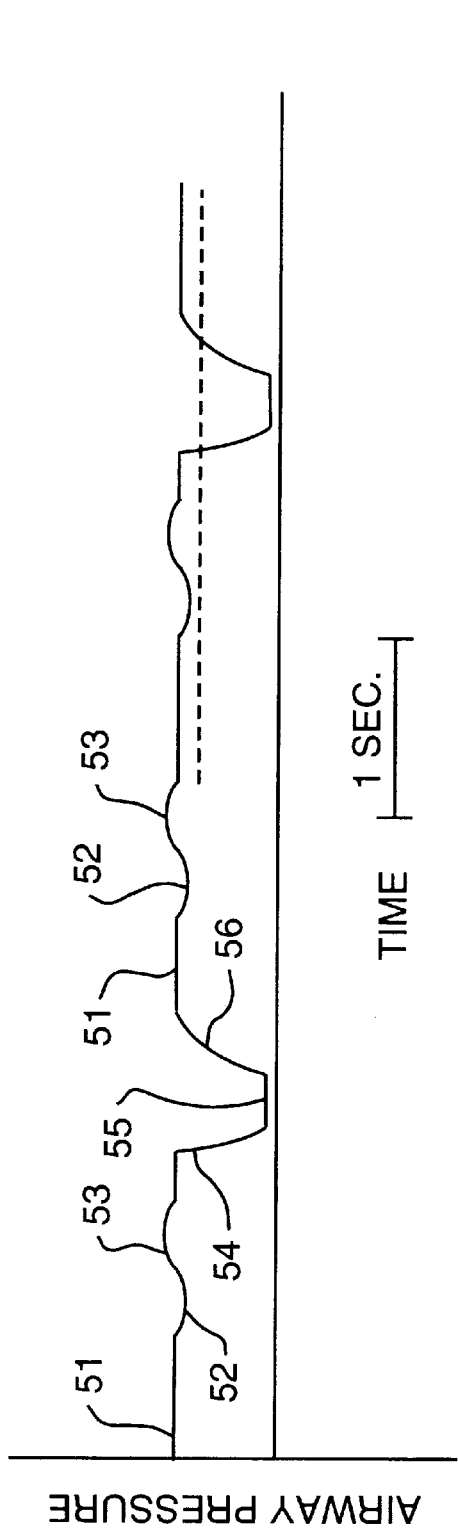
FIG. 5 is a graph of airway pressure vs. time representative of the use of the apneustic anesthesia ventilator of the present invention.
Figure 6:
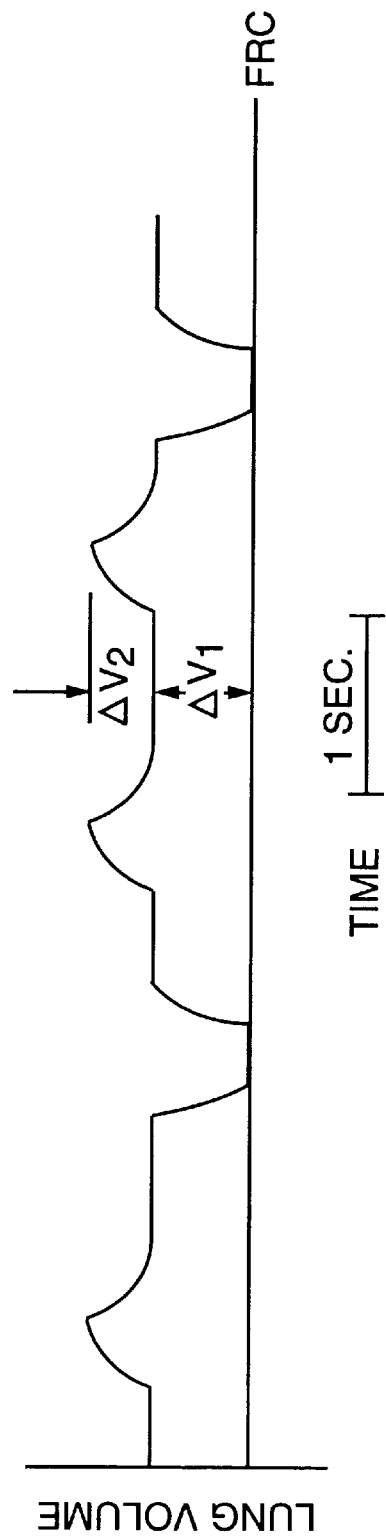
FIG. 6 is a graph of airway volume vs. time representative of the use of the apneustic anesthesia ventilator of the present invention.

As shown in FIG. 5, apneustic ventilation is created by elevation of lung volume and airway pressure above ambient 51. Slight deflection downward 52 and upward 53 of the airway pressure pattern indicates spontaneous inspiration and exhalation. Such fluctuation is minimized by limitation of flow resistance by both inspiratory 38 and expiratory 39 valve functions. The amount of gas drawn from the bellows 31 is $\Delta V_2$ in FIG. 3. Significant decline in airway pressure 54 is created by decompression of the space surrounding the concertina bag 31, within the rigid, translucent container 32, as determined by the release pressure of the AAV control 40. Such decompression results in gas exiting the patient's lung to the anesthesia breathing circuit in an amount equivalent to $\Delta V_1$ indicated in FIG. 3. After approximately 1 to 1.5 seconds of low pressure 55, repressurization of the space surrounding the concertina bag results in reapplication of pressure 56 and reinstitution of lung volume, above FRC. The mean airway pressure is shown by the dashed line in FIG. 5. The peak airway pressure illustrated in FIG. 5 is lower than the peak airway pressures shown in FIG. 2.

EXAMPLE

Operation of the AAV apparatus of the present invention was studied as follows. Nonsedated ASA physical status I and II patients scheduled for general anesthesia, intra-abdominal operations and insertion of an intra-arterial catheter for blood pressure monitoring, signed an Institutional Review Board approved consent. Patients with unstable cardiovascular function or severe obstructive lung disease were excluded from the study. Chest leads were attached to monitor EEG and heart rate was determined electronically. A probe was positioned around a finger tip and connected to a pulse oximeter for determination of oxygen saturation ($SpO_2$).

Anesthesia and neuromuscular blockade were induced with propofol (1 to 2 mg/kg IV) or thiopental (2 to 5 mg/kg IV) and succinylcholine (1.5 mg/kg) and the patients were intubated orotracheally. Anesthesia and neuromuscular blockade were maintained with isoflurane, nitrous oxide and oxygen and vecuronium. An intravenous narcotic was administered when appropriate. Patients were ventilated with conventional CMV using a VT ranging from 8 to 10 mL/kg and a respiratory rate (RR) sufficient to produce a $P_{ET}CO_2$ ranging from 30 to 35 mmHg. Inspired oxygen concentration was adjusted to maintain a $SpO_2$ of at least 90%. A thermistor was placed in the esophagus for monitoring temperature. A catheter was placed in the radial artery for determination of blood pressure and sampling blood for assay of pHa, $PaCO_2$, $PaO_2$, hemoglobin concentration and oxyhemoglobin saturation ($SaO_2$). A pneumotachograph was attached to the tracheal tube and connected to a pulmonary mechanics computer (BICORE, Irvine, Calif.) for determination of VT, RR, minute ventilation (VE), and peak and mean airway pressure (Paw). The sample tubing of a gas and anesthetic vapor monitor (Ultima, Datex Instrumentation, Helsinki, FN) was positioned between the pneumotach and anesthesia breathing circuit for determination of $FIO_2$, $P_{ET}CO_2$, end-tidal concentration of isoflurane and nitrous oxide, and minimum alveolar concentration (MAC) of inhalation anesthetic agents. The efficiency of ventilations was qualified as $PaCO_2 \cdot VE^{-1}$.

Baseline data were collected after heart rate, mean arterial blood pressure and MAC remained unchanged for 30 minutes. Patients were randomly assigned to receive alternate 20 minute trials of CMV (using the same characteristics as baseline) and AAV of the present invention. The respiratory rate during AAV was the same as during baseline. Tidal volume during AAV was titrated to produce a $P_{ET}CO_2$ two to three mmHg greater than the value observed during baseline CMV. AAV was provided with an anesthesia ventilator (Model Mark 4A, Bird Corporation, Palm Springs, Calif.) modified as shown in FIG. 3.

Data are summarized as mean±1SD. A carry-over of treatment effect (treatment-period interaction) was assessed by comparing the differences (mean±1SD) for the two treatment sequences. Student's t test for independent observations was used to compare the differences (mean±1SD) between the two treatment sequences. There was no significant treatment-period interaction, thus data were statistically compared using Student's t test for paired observations (two-tailed). Data obtained during alternate trials of AAV and CMV were compared.

Twenty patients (11 female, 9 male) 62±15 years old, weight 88±26 kg, underwent similar anesthesia care and operative procedures. End-tidal concentration of isoflurane (1.1±0.3), MAC (1.5±0.2), body temperature (35.7±0.5° C.) and hemoglobin concentration (10.8±1.5 gm/dL) were similar throughout the study, and inter-trial data were pooled for summary. There were no differences in cardiovascular function throughout the study, as shown in Table 1.

TABLE 1

Cardiovascular Function During Airway AAV and Controlled Mechanical Ventilation CMV in Patients Undergoing General Anesthesia

| Trial | HR (min$^{-1}$) | SAP (mmHg) | DAP (mmHg) | MAP (mmHg) |
|---|---|---|---|---|
| AAV | 70 ± 12 | 120 ± 23 | 70 ± 12 | 83 ± 18 |
| CMV | 72 ± 11 | 123 ± 23 | 64 ± 14 | 85 ± 17 |

Data are summarized as mean ± 1SD and inter-trial comparisons were performed using Student's t test. HR = heart rate, SAP = systolic arterial pressure, DAP = diastolic arterial pressure and MAP = mean arterial pressure.

Peak airway pressure was less when the patients were ventilated with AAV than when they received CMV, as shown in Table 2.

TABLE 2

Comparison of Peak Airway Pressure for AAV vs. CMV

| Trial | Peak Paw (cmH$_2$O) | Mean Paw (cmH$_2$O) | VT (mL) | RR (min$^{-1}$) | VE (L/min) |
|---|---|---|---|---|---|
| AAV | 13 ± 2* | 11 ± 3* | 612 ± 168* | 7 ± 1 | 4.0 ± 1.1* |
| CMV | 24 ± 5 | 8 ± 2 | 768 ± 166 | 7 ± 1 | 5.6 ± 1.1 |

Data are summarized as mean ± 1SD and inter-trial comparisons were performed with Student's t test (*p < 0.01 compared to CMV). Peak Paw = Peak airway pressure, Mean Paw = mean airway pressure, VT = tidal volume, RR = respiratory rate and VE = minute ventilation.

During AAV, peak airway pressure did not exceed 18 cm $H_2O$ in any patient, and was less than one-half that observed during CMV in six patients. Although mean airway pressure was greater when patients breathed with AAV, there were no adverse cardiovascular consequences.

Respiratory rate was similar by design, but comparable $PaCO_2$ was achieved with less tidal volume and VE during AAV compared to during CMV. Thus, AAV of the present invention improves the efficiency of ventilation, quantified as the $PaCO_2 \cdot VE^{-1}$, as shown in Table 3.

TABLE 3

Gas Exchange During AAV vs. CMV in Patients Undergoing General Anesthesia (FIO$_2$ = 0.33 ± 0.08)

| Trial | pHa | PaCO$_2$ (mmHg) | PaO$_2$ (mmHg) | SaO$_2$ (%) | P$_{(a-ET)}$CO$_2$ (mmHg) | PaCO$_2$/VE (mmHg/Lmin$^{-1}$) |
|---|---|---|---|---|---|---|
| AAV | 7.40 ± 0.04 | 38.6 ± 3.0 | 110 ± 42 | 95.6 ± 3.7 | 1.5 ± 0.9* | 10.4 ± 2.8* |
| CMV | 7.42 ± 0.04 | 37.0 ± 2.2 | 117 ± 40 | 96.1 ± 3.0 | 5.1 ± 2.3 | 7.1 ± 1.6 |

Data are summarized as mean ± 1SD and inter-trial comparisons were performed with Student's t test (*p < 0.01 compared to CMV). pHa = arterial blood pH, PaO$_2$ = partial pressure of oxygen in arterial blood, SaO$_2$ arterial blood oxyhemoglobin saturation, P$_{(a-ET)}$CO$_2$ = partial pressure of carbon dioxide in arterial blood minus end-tidal gas, and PaCO$_2$/VE = ratio of PaCO$_2$ and minute ventilation.

There were no differences in $FIO_2$, and arterial blood gas tensions, pHa, and oxyhemoglobin saturation were unchanged throughout the study. The $P_{(a-ET)}CO_2$ always was lower during AAV (1.5±0.9 mmHg), than during CMV (5.1±2.3 mmHg) (p<0.0001), and never was greater than 3.5 mmHg. During CMV, $P_{(a-ET)}CO_2$ ranged from as low as 3.0 mmHg to as high as 9.5 mmHg.

In accordance with the method of the present invention, the minute ventilation required to achieve similar alveolar ventilation as reflected by $PaCO_2$ was lower when patients were ventilated with AAV than CMV. The lower minute ventilation during AAV resulted from a lower tidal volume. Presumably, anatomical dead space was nearly constant. Therefore, comparable $PaCO_2$ and a narrower $P_{(a-PE)}CO_2$ with less minute ventilation were evidence for reduced alveolar dead space ventilation during AAV. Since alveolar dead space ventilation was less when patients were ventilated with AAV, $P_{ET}CO_2$ more accurately reflected $PaCO_2$ during AAV than during CMV. The observation that dead space ventilation is lower during AAV may be due to the significantly lower peak airway pressure during AAV. Although the mean airway pressure was greater during AAV, there were no apparent adverse cardiovascular consequences.

Functional residual capacity is known to be reduced about 15% to 18% after the induction of general anesthesia in supine patients. The reduction of FRC commences immediately after the induction of anesthesia and is not progressive. This effect is similar among anesthetic techniques and is independent of muscle paralysis. The mechanism underlying the reduction of FRC remains unclear. Atelectasis, increased abdominal and/or thoracic blood volume, increased activity of expiratory or decreased activity of inspiratory muscles, increased elastic recoil of the lungs or decreased outward recoil of the chest wall, or any combination of these may contribute to the reduction of FRC.

A decrease in resting lung volume is associated with a number of adverse physiologic consequences, including impaired lung mechanics, right-to-left intrapulmonary shunting of blood and ventilation and perfusion mismatching. Functional residual capacity may be restored to near normal with the application of continuous positive airway pressure. The change (Δ) in FRC affected by CPAP may be estimated in the following manner:

$$\Delta FRC = CPAP \times CLT$$

where CLT=lung-thorax compliance. Periodic release of CPAP causes lung volume to decline and the restoration of CPAP causes lung volume to increase, thus providing alveolar ventilation and excretion of carbon dioxide.

Fundamentally, AAV differs from other methods of positive pressure ventilation in that it is a CPAP system designed to increase resting lung volume, and to augment alveolar ventilation, when spontaneous ventilation is inadequate. The VT affected by AAV is determined by several factors, including release time, release pressure and lung-thorax compliance. The time required for gas to leave the lung during pressure release is determined by the CLT and resistance to gas flow. The product of these variables is the time constant for exhalation. As long as the release time exceeds three time constants the VT may be reflected as the product of CLT and release pressure.

Elevations in mean airway pressure during mechanical ventilation may depress cardiovascular function. Patients with low intravascular volume or compromised myocardial function are particularly susceptible to the adverse hemodynamic sequelae associated with positive pressure ventilation. Although mean airway pressure was higher when patients breathed with AAV compared to CMV, there were no apparent hemodynamic consequences.

Since mechanical ventilation during AAV is accomplished by decreasing airway pressure from a level of CPAP titrated to optimize lung mechanics, peak airway pressure does not exceed the CPAP level. Peak airway pressure was always lower in patients during AAV than when they breathed with CMV. Theoretically, the risk of ventilator-induced lung injury should be lower when peak airway pressure does not exceed the level of pressure necessary to optimize lung function.

The $P_{(a-ET)}CO_2$ during AAV was similar to that observed in spontaneously breathing patients. During spontaneous breathing, inspired gas is predominantly distributed to relatively well perfused alveoli in dependent lung regions and end-expired gas closely approximates alveolar gas. However, in anesthetized, paralyzed and mechanically ventilated patients, the inspired gas is preferentially distributed to poorly or nonperfused alveoli in non-dependent lung to units and end-expired gas represents significant alveolar dead space. During spontaneous breathing, the $P_{(a-ET)}CO_2$ may range from 1 to 3 mmHg. During CMV, the $P_{(a-ET)}CO_2$ may exceed 12 mmHg and is rarely less than 6 mmHg. When inspiration occurs from a lung volume less than FRC, the maldistribution of inspired air relative to perfusion is exaggerated. Thus, dead space ventilation is greater during CMV, particularly when the resting lung volume is reduced, which is the circumstance after induction of general anesthesia. Improved efficiency of ventilation as evidenced by an increased $PaCO_2 \cdot VE^{-1}$ during AAV versus CMV indicates that dead space ventilation was reduced when patients breathed with AAV. The lower peak airway pressure during AAV would explain a lower alveolar dead space in non-dependent lung regions.

Since the patients received continuous neuromuscular blockade, both CMV and AAV provided total ventilatory support. The efficiency of spontaneous breathing during operations not requiring neuromuscular blockade may be improved by the restoration of FRC with CPAP. Application of AAV to provide partial mechanical support of spontaneous breathing in patients unable to maintain eucapnia during general anesthesia may have several advantages over CMV, including lower mean intrathoracic (pleural) pressure, augmented venous return and improved cardiovascular performance, and better distribution of inspired gas flow resulting in improved ventilation-perfusion matching.

The present invention provides more efficient ventilation of patients undergoing general anesthesia with significantly lower peak airway pressure, compared to conventional CMV techniques. The improved efficiency of ventilation decreases the required minute ventilation and permits reduction of tidal volume and/or respiratory rate, thus reducing lung inflation frequency or magnitude, respectively. Thus, there is less respiratory movement and a potential improvement in technical conditions during intra-abdominal operations. During use of the apparatus of the present invention, $P_{(a-ET)}CO_2$ approximates the value observed during spontaneous breathing, rendering $P_{ET}CO_2$ a more accurate monitor of ventilation than during conventional techniques.

While a specific embodiment of the present invention has been described herein, it is to be understood that various changes, modifications and adaptations may be made without departing from the scope of the invention as set forth in the following claims.

What is claimed is:

1. A method of providing breathing gas to a patient during general anesthesia, the method comprising:
   providing a supply of breathing gas to the patient;
   controlling the volume of the breathing gas supplied to the patient at a level above the functional residual capacity of the patient;
   controlling the pressure of the breathing gas supplied to the patient to produce a substantially continuous positive airway pressure in the patient;
   allowing the patient to spontaneously respire causing a change in the lung volume of the patient while the volume of gas in the patient's lungs is above the functional residual capacity of the patient; and
   periodically reducing the pressure of the breathing gas supplied to the patient to facilitate expulsion of carbon dioxide-containing gas from the patient.

2. The method of claim 1, wherein the breathing gas comprises anesthesia gas.

3. The method of claim 1, further comprising providing a ventilator including a bellows having an interior volume in flow communication with the airway of the patient for controlling the volume of breathing gas supplied to the patient.

4. The method of claim 3, further comprising applying pressure to an exterior surface of the bellows to control the volume of breathing gas supplied to the patient.

5. The method of claim 4, further comprising periodically reducing the pressure applied to the exterior surface to substantially ambient pressure to thereby reduce the pressure of the breathing gas supplied to the patient.

6. The method of claim 1, wherein the volume of breathing gas supplied to the patient is periodically reduced to a level approximating the functional residual capacity of the patient.

7. The method of claim 6, further comprising maintaining the volume of breathing gas at the level approximating the functional residual capacity of the patient for a predetermined period of time.

8. The method of claim 7, wherein the periodic reduction of the volume of breathing gas occurs at substantially equal time intervals.

9. The method of claim 1, wherein the pressure of the breathing gas supplied to the patient is periodically reduced to a level approximating ambient atmospheric pressure.

10. The method of claim 9, further comprising maintaining the reduced pressure level of the breathing gas for a predetermined period of time.

11. The method of claim 10, wherein the periodic reduction of the breathing gas pressure occurs at substantially equal time intervals.

12. The method of claim 1, further comprising sensing the volume of the breathing gas supplied to the patient.

13. The method of claim 1, further comprising sensing the flow of breathing gas supplied to the patient and the flow of gas expelled from the patient.

14. The method of claim 1, further comprising determining an arterial blood carbon dioxide tension level of the patient by sensing end-tidal carbon dioxide expelled from the patient.

15. The method of claim 13, further comprising sensing the pressure of the breathing gas supplied to the patient.

16. Apparatus for providing breathing gas to a patient during general anesthesia comprising:
   supply means for providing breathing gas to the patient;
   control means for supplying breathing gas to the patient at a volume above the functional residual capacity of the patient, for controlling the pressure of the breathing gas supplied to the patient to produce a substantially continuous positive airway pressure in the patient, and for periodically reducing the pressure of the breathing gas supplied to the patient to facilitate expulsion of carbon dioxide-containing gas from the patient; and
   spontaneous breathing means for allowing the patient to spontaneously respire causing a change in the lung volume of the patient while the volume of gas in the patient's lungs is above the functional residual capacity of the patient.

17. The apparatus of claim 16, further comprising a bellows having an interior volume in flow communication with the airway of the patient for controlling the volume of breathing gas supplied to the patient.

18. The apparatus of claim 17, wherein the interior volume of the bellows is varied by controlling pressure applied to an exterior surface of the bellows.

19. The apparatus of claim 18, wherein the pressure applied to the exterior surface of the bellows is substantially equal to a continuous positive airway pressure of the patient.

20. The apparatus of claim 19, wherein the pressure applied to the exterior surface of the bellows is periodically reduced to substantially ambient pressure below the continuous positive airway pressure of the patient.

21. The apparatus of claim 16, further comprising means for periodically reducing the volume of breathing gas supplied to the patient to a level approximating the functional residual capacity of the patient.

22. The apparatus of claim 21, further comprising means for maintaining the volume of breathing gas at the level approximating the functional residual capacity of the patient for a predetermined period of time.

23. The apparatus of claim 21, wherein the means for periodically reducing the volume of breathing gas includes means for reducing the volume at substantially equal time intervals.

24. The apparatus of claim 16, wherein the means for controlling the pressure of the breathing gas supplied to the patient includes means for periodically reducing the pressure to a level approximating ambient atmospheric pressure.

25. The apparatus of claim 24, further comprising means for maintaining the reduced pressure level of the breathing gas for a predetermined period of time.

26. The apparatus of claim 25, wherein the means for periodically reducing the breathing gas pressure includes means for reducing the pressure at substantially equal time intervals.

27. The apparatus of claim 16, further comprising means for sensing the volume of the breathing gas supplied to the patient.

28. The apparatus of claim 16, further comprising means for sensing the flow of breathing gas supplied to the patient and the flow of gas expelled from the patient.

29. The apparatus of claim 16, further comprising means for determining an arterial blood carbon dioxide tension level of the patient by sensing end-tidal carbon dioxide expelled from the patient.

30. The apparatus of claim 16, further comprising means for sensing the pressure of the breathing gas supplied to the patient.

31. The apparatus of claim 16, wherein the supply means comprises a semi-closed anesthesia gas delivery system.

32. The apparatus of claim 30, wherein the semi-closed anesthesia gas delivery system comprises a circle $CO_2$ absorber system.

33. The apparatus of claim 16, wherein the supply means comprises a closed anesthesia gas delivery system.

34. A method of providing breathing gas to a patient during general anesthesia, the method comprising:

provide a supply of breathing gas to the patient;

controlling the volume of the breathing gas supplied to the patient at a level above the functional residual capacity of the patient;

allowing the patient to spontaneously respire causing a change in the lung volume of the patient while the volume of gas in the patient's lungs is above the functional residual capacity of the patient; and periodically reducing the pressure of the breathing gas supplied to the patient to effect a lung volume approximating the functional residual capacity of the patient to facilitate expulsion of carbon dioxide-containing gas from the patient.

35. Apparatus for providing breathing gas to a patient during general anesthesia comprising:

supply means for providing breathing gas to the patient;

control means for supplying breathing gas to the patient at a volume above the functional residual capacity of the patient, for periodically reducing the volume of breathing gas supplied to the patient to a level approximating the functional residual capacity of the patient, and for periodically reducing the pressure of the breathing gas supplied to the patient to facilitate expulsion of carbon dioxide-containing gas from the patient; and spontaneous breathing means for allowing the patient to spontaneously respire causing a change in the lung volume of the patient while the volume of gas in the patient's lungs is above the functional residual capacity of the patient.

* * * * *

UNITED STATES PATENT AND TRADEMARK OFFICE
CERTIFICATE OF CORRECTION

PATENT NO.     : 6,123,072
DATED          : September 26, 2000
INVENTOR(S)    : John B. Downs It is certified that error appears in the above-identified patent and that said Letters Patent is hereby corrected as shown below:

Column 12,
Line 21, remove "to" after "lung".

Signed and Sealed this

Second Day of April, 2002

Attest:

Attesting Officer

JAMES E. ROGAN
Director of the United States Patent and Trademark Office